US012006247B2

(12) United States Patent
Signer-Apel et al.

(10) Patent No.: US 12,006,247 B2
(45) Date of Patent: Jun. 11, 2024

(54) LITHIUM SILICATE MATERIALS

(71) Applicant: Ivoclar Vivadent AG, Schaan (LI)

(72) Inventors: Elke Signer-Apel, Oberschan (CH); Wolfram Höland, Schaan (LI); Marcel Schweiger, Chur (CH); Christian Ritzberger, Nenzing (AT); Harald Bürke, Frastanz (AT); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 229 days.

(21) Appl. No.: 17/233,898

(22) Filed: Apr. 19, 2021

(65) Prior Publication Data
US 2021/0238082 A1    Aug. 5, 2021

Related U.S. Application Data

(60) Continuation of application No. 16/284,563, filed on Feb. 25, 2019, now Pat. No. 10,981,823, which is a continuation of application No. 15/255,443, filed on Sep. 2, 2016, now Pat. No. 10,214,443, which is a continuation of application No. 14/567,173, filed on Dec. 11, 2014, now Pat. No. 9,434,639, which is a continuation of application No. 13/940,362, filed on Jul. 12, 2013, now Pat. No. 8,940,651, which is a continuation of application No. 13/175,370, filed on Jul. 1, 2011, now Pat. No. 8,546,280, which is a continuation of application No. 12/944,578, filed on Nov. 11, 2010, now Pat. No. 7,993,137, which is a continuation of application No. 12/253,437, filed on Oct. 17, 2008, now Pat. No. 7,871,948, which is a division of application No. 11/348,053, filed on Feb. 6, 2006, now Pat. No. 7,452,836.

(30) Foreign Application Priority Data

Feb. 8, 2005    (EP) ..................................... 05002588
Jun. 20, 2006   (DE) ........................ 102005028637.2

(51) Int. Cl.
| | | |
|---|---|---|
| C03C 10/00 | (2006.01) |
| A61C 5/70 | (2017.01) |
| A61C 5/77 | (2017.01) |
| A61C 8/00 | (2006.01) |
| A61C 13/00 | (2006.01) |
| A61C 13/08 | (2006.01) |
| A61C 13/083 | (2006.01) |
| A61K 6/78 | (2020.01) |
| A61K 6/804 | (2020.01) |
| A61K 6/807 | (2020.01) |
| A61K 6/818 | (2020.01) |
| A61K 6/833 | (2020.01) |
| C01B 33/32 | (2006.01) |
| C03B 32/02 | (2006.01) |
| C03C 3/097 | (2006.01) |
| C03C 4/00 | (2006.01) |

(52) U.S. Cl.
CPC ............ *C03C 10/0027* (2013.01); *A61C 5/70* (2017.02); *A61C 5/77* (2017.02); *A61C 8/0001* (2013.01); *A61C 8/0012* (2013.01); *A61C 8/0048* (2013.01); *A61C 13/0004* (2013.01); *A61C 13/0006* (2013.01); *A61C 13/0022* (2013.01); *A61C 13/082* (2013.01); *A61C 13/083* (2013.01); *A61K 6/78* (2020.01); *A61K 6/804* (2020.01); *A61K 6/807* (2020.01); *A61K 6/818* (2020.01); *A61K 6/833* (2020.01); *C01B 33/32* (2013.01); *C03B 32/02* (2013.01); *C03C 3/097* (2013.01); *C03C 4/0021* (2013.01); *C03C 10/0045* (2013.01); *C03C 10/0054* (2013.01); *Y10T 83/04* (2015.04); *Y10T 409/303752* (2015.01)

(58) Field of Classification Search
CPC ............ C03C 10/0027; C03C 10/0045; C03C 10/0054; C03C 4/0021
See application file for complete search history.

(56) References Cited

U.S. PATENT DOCUMENTS

| | | | |
|---|---|---|---|
| 2,684,911 | A | 7/1954 | Stookey |
| 3,022,180 | A | 2/1962 | Morrissey et al. |
| 3,252,778 | A | 5/1966 | Goodmann et al. |
| 3,287,201 | A | 11/1966 | Chisholm et al. |
| 3,006,775 | A | 10/1969 | Chen |
| 3,679,464 | A | 7/1972 | Eppler |
| 3,804,608 | A | 4/1974 | Gaskell et al. |

(Continued)

FOREIGN PATENT DOCUMENTS

| | | |
|---|---|---|
| CA | 2252660 | 5/1999 |
| DE | 1696473 | 8/1970 |
| DE | 2451121 | 5/1975 |
| DE | 3015529 | 6/1980 |
| DE | 294619 | 11/1980 |
| DE | 4303458 | 1/1994 |
| DE | 19647739 | 3/1998 |
| DE | 19750794 | 6/1999 |

(Continued)

OTHER PUBLICATIONS

Apel et al., Influence of ZrO2 on the crystallization and properties of lithium disilicate glass-ceramics derived from multi-component system, Journal of European Ceramic Society, 2007, 27, 1571-1577.

(Continued)

*Primary Examiner* — Bryan D. Ripa
*Assistant Examiner* — Cameron K Miller
(74) *Attorney, Agent, or Firm* — Hodgson Russ LLP

(57) ABSTRACT

Lithium silicate materials are described which can be easily processed by machining to dental products without undue wear of the tools and which subsequently can be converted into lithium silicate products showing high strength.

5 Claims, No Drawings

(56) References Cited

U.S. PATENT DOCUMENTS

| | | |
|---|---|---|
| 3,816,704 A | 6/1974 | Borom et al. |
| 3,977,857 A | 8/1976 | Mattox |
| 4,155,888 A | 5/1979 | Mooth et al. |
| 4,189,325 A | 2/1980 | Barrett et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,671,770 A | 6/1987 | Bell et al. |
| 4,755,488 A | 7/1988 | Nagashima |
| 4,798,536 A | 1/1989 | Katz |
| 4,963,707 A | 10/1990 | Zyokou et al. |
| 4,977,114 A | 12/1990 | Horinouchi et al. |
| 5,045,402 A | 9/1991 | Adams, Jr. et al. |
| 5,176,961 A | 1/1993 | Crooker et al. |
| 5,217,375 A | 6/1993 | Oden et al. |
| 5,219,799 A | 6/1993 | Beall et al. |
| 5,432,130 A | 7/1995 | Rheinberger et al. |
| 5,507,981 A | 4/1996 | Petticrew |
| 5,618,763 A | 4/1997 | Frank et al. |
| 5,628,564 A | 5/1997 | Nenyel |
| 5,641,347 A | 6/1997 | Grabowski et al. |
| 5,691,256 A | 11/1997 | Taguchi et al. |
| 5,698,019 A | 12/1997 | Frank et al. |
| 5,698,482 A | 12/1997 | Frank |
| 5,702,514 A | 12/1997 | Petticrew |
| 5,707,777 A | 1/1998 | Aoai et al. |
| 5,872,069 A | 2/1999 | Abe |
| 5,874,376 A | 2/1999 | Taguchi et al. |
| 5,938,959 A | 8/1999 | Wang |
| 5,968,856 A | 10/1999 | Schweiger et al. |
| 6,022,819 A | 2/2000 | Panzera et al. |
| 6,048,589 A | 4/2000 | Suzuki |
| 6,066,584 A | 5/2000 | Krell et al. |
| 6,095,682 A | 8/2000 | Hollander |
| 6,106,747 A | 8/2000 | Wohlwend |
| 6,119,483 A | 9/2000 | Takahashi et al. |
| 6,121,175 A | 9/2000 | Drescher et al. |
| 6,157,004 A | 12/2000 | Bizzio |
| 6,163,020 A | 12/2000 | Bartusch et al. |
| 6,174,827 B1 | 1/2001 | Goto |
| 6,252,202 B1 | 6/2001 | Zychek |
| 6,267,595 B1 | 7/2001 | Gratz |
| 6,270,876 B1 | 8/2001 | Abe et al. |
| 6,280,863 B1 | 8/2001 | Frank et al. |
| 6,287,121 B1 | 9/2001 | Guiot et al. |
| 6,342,458 B1 | 1/2002 | Schweiger et al. |
| 6,376,397 B1 | 4/2002 | Petticrew |
| 6,420,288 B2 | 7/2002 | Schweiger et al. |
| 6,441,346 B1 | 8/2002 | Zychek |
| 6,455,451 B1* | 9/2002 | Brodkin ............... A61K 6/818 264/16 |
| 6,485,849 B2 | 11/2002 | Petticrew |
| 6,514,893 B1 | 2/2003 | Schweiger et al. |
| 6,517,623 B1 | 2/2003 | Brodkin et al. |
| 6,593,257 B1 | 7/2003 | Nagata |
| 6,802,894 B2 | 10/2004 | Brodkin et al. |
| 6,818,573 B2 | 11/2004 | Petticrew |
| 7,162,321 B2 | 1/2007 | Luthardt et al. |
| 7,166,548 B2 | 1/2007 | Apel et al. |
| 7,316,740 B2 | 1/2008 | Schweiger et al. |
| 7,452,836 B2 | 11/2008 | Apel et al. |
| 7,655,586 B1 | 2/2010 | Brodkin et al. |
| 7,806,694 B2 | 10/2010 | Brodkin et al. |
| 7,816,291 B2 | 10/2010 | Schweiger et al. |
| 7,867,930 B2 | 1/2011 | Apel et al. |
| 7,867,933 B2 | 1/2011 | Apel et al. |
| 7,871,948 B2 | 1/2011 | Apel et al. |
| 7,892,995 B2 | 2/2011 | Castillo |
| 7,993,137 B2 | 8/2011 | Apel et al. |
| 8,042,358 B2 | 10/2011 | Schweiger et al. |
| 8,047,021 B2 | 11/2011 | Schweiger et al. |
| 8,444,756 B2 | 5/2013 | Schweiger et al. |
| 2001/0006174 A1 | 7/2001 | Brennan |
| 2002/0009600 A1 | 1/2002 | Peng |
| 2002/0010063 A1 | 1/2002 | Schweiger et al. |
| 2002/0022563 A1 | 2/2002 | Schweiger et al. |
| 2002/0031670 A1 | 3/2002 | Goto et al. |
| 2002/0035025 A1 | 3/2002 | Schweiger et al. |
| 2004/0182538 A1 | 9/2004 | Lambrecht |
| 2005/0098064 A1 | 5/2005 | Schweiger et al. |
| 2005/0127544 A1 | 6/2005 | Brodkin et al. |
| 2006/0082033 A1 | 4/2006 | Hauptmann et al. |
| 2006/0257823 A1 | 11/2006 | Pfeiffer et al. |
| 2006/0257824 A1 | 11/2006 | Pfeiffer et al. |
| 2007/0023971 A1 | 2/2007 | Saha et al. |
| 2008/0120994 A1 | 5/2008 | Schweiger et al. |
| 2008/0199823 A1 | 8/2008 | Miller |
| 2009/0023574 A1 | 1/2009 | Holand et al. |
| 2009/0038344 A1 | 2/2009 | Apel et al. |
| 2009/0038508 A1 | 2/2009 | Apel et al. |
| 2009/0042166 A1 | 2/2009 | Craig et al. |
| 2009/0256274 A1 | 10/2009 | Castillo |
| 2009/0258778 A1 | 10/2009 | Castillo |
| 2010/0083706 A1 | 4/2010 | Castillo |
| 2011/0030423 A1 | 2/2011 | Johannes et al. |
| 2011/0256409 A1 | 10/2011 | Ritzberger et al. |
| 2012/0094822 A1 | 4/2012 | Castillo |
| 2012/0148988 A1 | 6/2012 | Castillo |
| 2012/0309607 A1 | 6/2012 | Durschang |
| 2012/0248642 A1 | 10/2012 | Ritzberger et al. |

FOREIGN PATENT DOCUMENTS

| | | |
|---|---|---|
| EP | 0231773 | 8/1987 |
| EP | 536479 | 4/1993 |
| EP | 536572 | 4/1993 |
| EP | 0817597 | 1/1998 |
| EP | 0827941 | 3/1998 |
| EP | 774933 | 6/2000 |
| EP | 1127564 | 8/2001 |
| EP | 1152641 | 11/2001 |
| EP | 1422210 | 5/2004 |
| EP | 1505041 | 2/2005 |
| EP | 1688398 | 8/2006 |
| GB | 752243 | 7/1956 |
| GB | 2284655 | 6/1995 |
| JP | 325080 | 8/1953 |
| JP | 5094017 | 10/1974 |
| JP | 05208846 | 8/1993 |
| JP | 7187710 | 7/1995 |
| JP | 9501092 | 2/1997 |
| JP | 10101409 | 4/1998 |
| JP | 10323354 | 12/1998 |
| JP | 1174418 | 3/1999 |
| JP | 11074418 | 3/1999 |
| JP | 11314938 | 11/1999 |
| JP | 2001035417 | 2/2001 |
| JP | 2001288027 | 10/2001 |
| JP | 200553776 | 3/2005 |
| JP | 2005062832 | 3/2005 |
| JP | 2008515549 | 5/2008 |
| WO | 199532678 | 12/1995 |
| WO | 0228802 | 4/2002 |
| WO | 0247616 | 6/2002 |
| WO | 03035014 | 1/2003 |
| WO | 2006042046 | 4/2006 |
| WO | 2007028787 | 3/2007 |
| WO | 2012143137 | 10/2012 |

OTHER PUBLICATIONS

McMillan et al., The Structure and Properties of a Lithium Zinc Silicate Glass-Ceramic, Journal of Material Science 1966, I. 269-279.

Deubener et al., Induction time analysis of nucleation and crystal grown in di- and metasilicate glasses, Journal of Non-Crystalline Solids 1993, 163, 1-12.

Holand et al., Glass-ceramic technology, American Chemical Society 2002, Westerville OH, USA.

Holand et al., Control of nucleation in glass ceramics, Phil. Trans. Soc. Lond. A 2003, 361, 575-589.

(56) References Cited

OTHER PUBLICATIONS

Holand et al., Principles and phenomena of bioengineering with glass-ceramics of dental restoration, Journal of the European Ceramics Society 2007, 27, 1571-1577.7.

Ivoclar Vivadent, Inc., IPS e.max lithium disilicate, 627329, Rev. Feb. 2009.

Durschang, Report of Results, Fraunhofer Institute for Silicate Research ISC Glass and Mineral Materials, 2015.

Kalinina, A.M., et al., Crystallization Products of Lithium Silicate Glasses, The Structure of Glass, vol. 3: Catalyzed Crystallization of Glass, E.B. Uvarov, 1964, pp. 53-64.

Stookey, S.D., "Chemical Machining of Photosensitive Glass," Ind. Eng. Chem. 45:115-118 (1993).

Montedo et al., Low Thermal Expansion Sintered LZSA Glass Ceramics, American Ceramic Society Bulletin, 2008, vol. 87, Issue 7, pp. 34-40.

Von Clausburch et al., "The effect of P2O5 on the Crystallization and Microstructure of Glass-Ceramics in the SiO2—LiO2—K2O—ZnO—P2O5 System," J. of Non-Crystalline Solids 263&264, pp. 388-394 (2000).

Giassi et al., "Injection Moulding of LiO2—ZrO2—SiO2—Al2O3 (LZSA) Glass Ceramics," Glass Technol., 46(3), 277-280 (2005).

Borom, et al., "Strength and Microstructure in Lithium Disilicate Glass Ceramics," J. Am. Ceram. Soc. 58 (9-10): 285-391 (1975).

de Oliveira et al., "Sintering and Crystalization of a Glass Powder in the Li2O—ZrO2—SiO2 System," J. Am. Ceramic Soc. 81(3):777-780 (1998).

Von Clausburch et al., "Effect of ZnO on the Crystallization, Microstructure, and Properties of Glass-Ceramics in the SiO2=Li2O—K2O—P2O5 System," Glastech. Ber. Glass. Sci. Technol. 74(8):223-229 (2001).

Sundh et al., Fracture resistance of yttrium oxide partially-stabilized zirconia all-ceramic bridges after veneering and mechanical fatigue testing. Dental Materials (2005) 21, 476-482.

European Search Report for EP Application No. 10171839.3, dated Jan. 25, 2011.

http://en.wikipedia.org/wiki/Nucleation Sep. 20, 2012.

\* cited by examiner

LITHIUM SILICATE MATERIALS

CROSS-REFERENCE TO RELATED APPLICATIONS

This application is a continuation of U.S. application Ser. No. 16/284,563, filed on Feb. 25, 2019, which is a continuation of U.S. application Ser. No. 15/255,443, filed on Sep. 2, 2016, now U.S. Pat. No. 10,214,443, issued on Feb. 26, 2019, which is a continuation of U.S. application Ser. No. 14/567,173, filed on Dec. 11, 2014, now U.S. Pat. No. 9,434,639, issued on Sep. 6, 2016, which is a continuation of U.S. application Ser. No. 13/940,362, filed on Jul. 7, 2013, now U.S. Pat. No. 8,940,651, issued on Jan. 27, 2015, which is a continuation of U.S. application Ser. No. 13/175,370, filed on Jul. 1, 2011, now U.S. Pat. No. 8,546,280, issued on Oct. 1, 2013, which is a continuation of U.S. application Ser. No. 12/944,578, filed on Nov. 11, 2010, now U.S. Pat. No. 7,993,137, issued on Aug. 9, 2011, which is a continuation of U.S. application Ser. No. 12/253,437, filed on Oct. 17, 2008, now U.S. Pat. No. 7,871,948, issued on Jan. 18, 2011, which is a divisional of U.S. application Ser. No. 11/348,053, filed on Feb. 6, 2006, now U.S. Pat. No. 7,452,836, issued on Nov. 18, 2008, which claims priority to European Patent Application No. EP 05002588.1, filed on Feb. 8, 2005, and to German Patent Application No. 10 2005 028 637.2, filed on Jun. 20, 2005, each of which are herein incorporated by reference in their entirety.

FIELD OF THE INVENTION

The invention primarily relates to lithium silicate materials which can be easily shaped by machining and subsequently converted into shaped products with high strength.

BACKGROUND OF THE INVENTION

There is an increasing demand for materials which can be processed into dental restorative products, such as crowns, inlays and bridges, by means of computer controlled milling machines. Such CAD/CAM methods are very attractive as they allow to provide the patient quickly with the desired restoration. A so-called chair-side treatment is thus possible for the dentist.

However, materials suitable for processing via computer aided design/computer aided machining (CAD/CAM) methods have to meet a very specific profile of properties.

First of all, they need to have in the finally prepared restoration appealing optical properties, such as translucence and shade, which imitate the appearance of the natural teeth. They further need to show high strength and chemical durability so that they can take over the function of the natural tooth material and maintain these properties over a sufficient period of time while being permanently in contact with fluids in the oral cavity which can even be aggressive, such as acidic in nature.

Secondly and very importantly, it should be possible to machine them in an easy manner into the desired shape without undue wear of the tools and within short times. This property requires a relatively low strength of the material and is therefore in contrast to the desired properties mentioned above for the final restoration.

The difficulty of combining the properties of low strength in the stage of the material to be processed and a high strength of the final restoration is reflected by the known materials for a CAD/CAM processing which are in particular with respect to an easy machinability unsatisfactory.

DE-A-197 50 794 discloses lithium disilicate glass ceramics which are primarily intended to be shaped to the desired geometry by a hot-pressing process wherein the molten material is pressed in the viscous state. It is also possible for these materials to be shaped by computer aided milling processes. However, it has been shown that the machining of these materials results in a very high wear of the tools and very long processing times. These disadvantages are caused by the high strength and toughness primarily imparted to the materials by the lithium disilicate crystalline phase. Moreover, it has been shown that the machined restorations show only a poor edge strength. The term "edge strength" refers to the strength of parts of the restoration having only a small thickness in the range of few ¹/₁₀ mm.

Further approaches of achieving easy machinability together with a high strength of the final restoration have also been made. EP-B-774 993 and EP-B-817 597 describe ceramic materials on the basis of $Al_2O_3$ or $ZrO_2$ which are machined in an unsintered state which is also referred to as "green state". Subsequently, the green bodys are sintered to increase the strength. However, these ceramic materials suffer from a drastical shrinkage of up to 50% by volume (or up to 30% as linear shrinkage) during the final sintering step. This leads to difficulties in preparing the restorations with exactly the dimensions as desired. The substantial shrinkage represents a particular problem if complicated restorations are manufactured, such as a multi-span bridge.

From S. D. Stookey: "Chemical Machining of Photosensitive Glass", Ind. Eng. Chem., 45, 115-118 (1993) and S. D. Stookey: "Photosensitively Opacifiable Glass" U.S. Pat. No. 2,684,911 (1954) it is also known that in lithium silicate glass ceramics a metastable phase can be formed at first. For example in photosensitive glass ceramics (Fotoform®, Foto-Ceram®) Ag-particles are formed using UV-light. These Ag-particles serve as crystallization agent in a lithium metasilicate phase. The areas which were exposed to light are in a subsequent step washed out by diluted HF. This procedure is possible since the solubility of the lithium metasilicate phase in HF is much higher than the solubility of the parent glass. The glass portion remaining after said solubilizing process (Fotoform®) can be transferred into a lithium disilicate glass ceramic (FotoCeram®) by an additional heat treatment.

Also investigations of Borom, e.g. M.-P. Borom, A. M. Turkalo, R. H. Doremus: "Strength and Microstructure in Lithium Disilicate Glass-Ceramics", J. Am. Ceram. Soc., 58, No. 9-10, 385-391 (1975) and M.-P. Borom, A. M. Turkalo, R. H. Doremus: "Verfahren zum Herstellen von Glaskeramiken" DE-A-24 51 121 (1974), show that a lithium disilicate glass ceramic can in the first instance crystallize in varying amounts as metastable lithium metasilicate phase. However, there also exist compositions which crystallize in the form of the disilicate phase from the beginning and the metasilicate phase is not present at all. A systematic investigation of this effect has not become known. From the investigations of Borom it is also known that the glass ceramic which contains lithium metasilicate as the main phase has a reduced strength compared to the one of a glass ceramic which only contains a lithium disilicate phase.

It has further been found out that the presence of ZnO in lithium silicate glass ceramics of the prior art is undesirable especially when highly translucent dental restorations are to be produced. Under such circumstances, the strong opalescent effect caused by ZnO is apparent and results in unacceptable optical properties for a restoration which is to imitate the natural tooth material.

SUMMARY OF THE INVENTION

It is, therefore, an object of the present invention to eliminate these disadvantages and in particular to provide a material which can be easily shaped by computer-aided milling and trimming processes and can subsequently be converted into a high-strength dental product which also displays a high chemical durability and excellent optical properties and exhibits a drastically reduced shrinkage during said final conversion, and achieves all these properties without the need for ZnO as a component.

This object is achieved by the lithium silicate glass ceramic according to the invention.

DETAILED DESCRIPTION OF THE INVENTION

It has surprisingly been shown that by using a starting glass of a very specific composition and a specific process it is possible to provide in particular a glass ceramic which has metastable lithium metasilicate ($Li_2SiO_3$) as main crystalline phase rather than lithium disilicate ($Li_2Si_2O_5$). This lithium metasilicate glass ceramic has a low strength and toughness and hence can be easily machined into the shape of even complicated dental restorations, but can after such machining be converted by a heat treatment into a lithium disilicate glass ceramic product with outstanding mechanical properties, excellent optical properties, in particular a strongly reduced opalescence, and very good chemical stability thereby undergoing only a very limited shrinkage.

The lithium silicate glass ceramic according to the invention comprises the following components:

| Component | wt.-% |
| --- | --- |
| $SiO_2$ | 64.0-75.0, in particular 64.0-73.0 |
| $Li_2O$ | 13.0-17.0 |
| $K_2O$ | 2.0-5.0 |
| $Al_2O_3$ | 0.5-5.0 |
| Nucleating agent | 2.0-5.0 |
| Me(II)O | 0-3.0 | with Me(II)O being selected from at least one of CaO, BaO, MgO and SrO, and comprises less than 0.1 wt. % of ZnO.

It is preferred that the glass ceramic is essentially free of ZnO.

It is surprising that even without presence of ZnO the glass ceramic according to the invention fulfils the mentioned multiple requirements. This was possible by the selection of the other components and their amounts and preferably by the ratios of some of these components to each other.

Preferred glass ceramics are those which comprise lithium metasilicate as main crystalline phase. Such glass ceramics are also referred to in the following as lithium metasilicate glass ceramics.

It has also been found out to be beneficial if the glass ceramic comprises 0 to 2.0 and preferably 0 to 1.5 wt. % of Me(II)O. Me(II)O is in particular selected from at least one of Cao and MgO. Particularly preferred glass ceramics comprise 0.1 to 1.0 wt. % of MgO.

The nucleating agent is preferably at least one of $P_2O_5$ and compounds of the elements Pt, Ag, Cu and W. It serves to induce formation of lithium metasilicate crystalls and is preferably $P_2O_5$.

Further, it was shown that a specific molar ratio of $SiO_2$ to $Li_2O$ serves to ensure that upon the necessary heat treatment of a corresponding starting glass mainly lithium metasilicate and lithium disilicate, respectively, is produced. This is of particular importance. While a lithium metasilicate glass ceramic essentially free of lithium disilicate results in particular in an excellent machinability, a lithium disilicate restoration essentially free of the easily dissolvable lithium metasilicate has a very good chemical stability.

Thus, it was found preferable that the molar ratio of $SiO_2:Li_2O$ is at least 2.2:1, preferably at least 2.3:1, and most preferred in the range of 2.3:1 to 2.5:1.

Moreover, investigations revealed that the molar ratio of $Al_2O_3:K_2O$ is of significance for obtaining the desired tranclucence and the predominant crystallization of lithium metasilicate.

It is preferred that the molar ratio of $Al_2O_3:K_2O$ is in the range of 1:0.5 to 1:2.0 and preferably is from 1:1 to 1:2.0.

There also exist preferred ranges for the amounts of components of the glass ceramic according to the invention. These can be used independently from each other.

It is preferred that the glass ceramic comprises 2.5 to 5.0 wt. % of $Al_2O_3$.

It is also preferred that the glass ceramic comprises 70.0 to 73.0 wt. % of $SiO_2$.

It is also preferred that the glass ceramic comprises 0 to 4.0, preferably 0.1 to 4.0, more preferably 1.0 to 4.0 and most preferred 1.5 to 3.0 wt. % of $ZrO_2$. If the emphasis is on the achieving of a high strength of the final lithium disilicate ceramic, then 0 to 2.0 wt. % to of $ZrO_2$ are advantageous.

It is further preferred that the glass ceramic comprises at least one of the following components in an amount of:

| Component | wt.-% |
| --- | --- |
| $Li_2O$ | 14.0-16.0 |
| $K_2O$ | 3.0-4.5 |
| coloring and fluorescent metal oxides | 0-7.5, preferably 0.5-3.5. |

The metal of the coloring and fluorescent metal oxides is preferably selected from group f-elements and in particular from the group of Ta, Tb, Y, La, Er, Pr, Ce, Ti, V, Fe and Mn. The colouring or fluorescent oxides ensure that the colour of the final dental product matches that of the natural tooth material of the patient in question.

Further, the glass ceramic may comprise as additional component $Na_2O$ in an amount of 0 to 2.0 wt.-%.

Additional components to enhance the technical processability of the glass may also be present. Such additional components may therefore be in particular compounds such as $B_2O_3$ and F which in general amount to 0 to 5.0% by weight.

Generally the amount of lithium metasilicate is 20 to 80 vol.-%. It has surprisingly been shown that a specific volume portion of lithium metasilicate should be present to achieve excellent processing properties. Thus, it is further preferred that the lithium metasilicate crystalline phase forms 20 to 50 vol % and in particular 30 to 40 vol % of the lithium silicate glass ceramic. Such a part of the volume leads to the crystals being present rather remote from each other and hence avoids a too high strength of the glass ceramic.

If the emphasis is on the achieving of a high strength of the lithium disilicate ceramic, then the lithium metasilicate phase preferably forms more than 50 and up to 80 vol. % of the lithium silicate glass ceramic.

The lithium metasilicate crystals are preferably of lamellar or platelet form. This leads to a very good machinability of the lithium metasilicate glass ceramic without use of high energy and without uncontrolled breaking. The latter aspect of uncontrolled breaking is for example known from glasses which are generally unsuitable for machining. It is assumed that the preferred morphology of the lithium metasilicate crystals is also responsible for the surprisingly high edge strength of products, e.g. complicated dental restorations, can be made from the lithium metasilicate glass ceramic according to the invention.

The lithium silicate glass ceramic according to the invention preferably is in the form of a blank. The blank usually takes the form of a small cylinder or a rectangular block. The exact form depends on the specific apparatus used for the desired computer-aided machining of the blank.

After the machining, the lithium silicate glass ceramic has preferably the shape of a dental restoration, such as an inlay, an onlay, a bridge, an abutment, a facing, a veneer, a facet, a crown, a partial crown, a framework or a coping.

A lithium silicate glass ceramic according to the invention which comprises lithium disilicate as main crystalline phase is a further preferred embodiment of the invention. It is preferred that this lithium disilicate glass ceramic is formed in a process wherein the lithium metasilicate of a glass ceramic according to the invention is converted to lithium disilicate crystals.

A dental product made from lithium disilicate glass ceramic according to the invention is a further preferred embodiment of the invention. It is preferred that such product is formed in a process wherein the lithium metasilicate of a glass ceramic according to the invention is converted to lithium disilicate crystals.

The lithium metasilicate glass ceramic according to the invention is preferably prepared by a process which comprises
(a) producing a starting glass containing the components of the glass ceramic,
(b) subjecting the starting glass to a first heat treatment at a first temperature to give a glass product which contains nuclei suitable for forming lithium metasilicate crystals,
(c) subjecting the glass product to a second heat treatment at a second temperature which is higher than the first temperature to obtain the lithium silicate glass ceramic with lithium metasilicate as the main crystalline phase.

In step (a), usually a melt of a starting glass is produced which contains the components of the glass ceramic. For this purpose a corresponding mixture of suitable starting materials, such as carbonates, oxides, and phosphates, is prepared and heated to temperatures of, in particular 1300 to 1600° C., for 2 to 10 hours. In order to obtain a particularly high degree of homogeneity, the glass melt obtained may be poured into water to form glass granules and the glass granules obtained are melted again.

It is further preferred that the melt of the starting glass is cooled, such as to room temperature, before subjecting it to step (b). The melt of the starting glass is also usually poured into a mould to form a starting glass blank.

In some cases it is convenient to control a cooling procedure such that it not only relaxes the glass, but also effects the first heat treatment of step (b).

In step (b) the starting glass is subjected to a first heat treatment at a first temperature to cause formation of nuclei for lithium metasilicate crystals. Preferably, this first heat treatment comprises heating the starting glass to a temperature of 500 to 600° C. for a period of about 10 minutes to 3 hours. This results in formation of a great number of nuclei that ensure a very satisfactory crystal growth. It also ensures that in the further processing after step (c) to give a lithium disilicate glass ceramic a very homogeneous lithium disilicate structure can be obtained.

It is also advantageous that the second heat treatment in step (c) comprises heating the glass product to a second temperature of 570° to 750° C., preferably 570 to 670° C., and more preferably to about 650° C.

It has further surprisingly been shown that relatively high temperatures lead to high amounts of lithium metasilicate which in turn lead to a high amount of lithium disilicate in the third heat treatment. Such high amounts of lithium disilicate impart a high strength to the ceramic. Thus, if the emphasis is on the achieving a high strength final product, then it is advantageous to carry out the second heat treatment at 680° to 720° C., and preferably 690° to 710° C. and more preferably about 700° C.

Depending on the specific composition of a selected starting glass, it is possible for the skilled person by means of differential scanning calorimetry (DSC) and x-ray diffraction analyses to determine suitable conditions in steps (b) and (c) to result in glass ceramics having the desired morphology and size of the crystals of lithium metasilicate. Moreover, these analyses allow also the identification of conditions avoiding or limiting the formation of undesirable other crystalline phases, such as of the high-strength lithium disilicate, or of cristobalite and lithium phosphate.

Usually, the starting glass of step (a), the glass product of step (b), or preferably the lithium metasilicate glass ceramic of step (c) is shaped to a desired geometry by machining or by hot pressing. The machining is in particular performed by grinding, trimming or milling and preferably controlled by a computer using CAD/CAM-based milling devices. This allows a so-called chair-side treatment of the patient by the dentist.

It is a particular advantage of the lithium metasilicate glass ceramic according to the invention that it can be shaped by machining without the undue wear of the tools observed with the tough and high-strength prior art materials. This is in particular shown by the easy possibility to polish and trim the glass ceramics according to the invention. Such polishing and trimming processes therefore require less energy and less time to prepare an acceptable product having the form of even very complicated dental restorations.

Further, the lithium metasilicate glass ceramic according to the invention can advantageously be processed to a lithium disilicate glass ceramic of high strength, which usually has a content of 50 to 85 vol. % and preferably 65 to 80 vol. % of crystalline lithium disilicate phase.

This is preferably effected by a process wherein the prepared lithium metasilicate glass ceramic of step (c) is subjected to a third heat treatment at a third temperature of 830 to 880° C. for a period of 10 to 60 minutes. This heat treatment can also be effected when hot-pressing the lithium metasilicate glass ceramic to achieve a shaping.

Thus, the lithium metasilicate glass ceramic can be further processed to the lithium dilsilicate glass ceramic of desired shape e.g. by both (i) CAD/CAM and a heat treatment or (ii) a hot-pressing. This is very advantageous for the user.

It is also possible to use for these purposes a corresponding lithium silicate glass which comprises nuclei suitable for formation of lithium metasilicate crystals. This glass is a precursor of the lithium metasilicate glass ceramic and the lithium disilicate glass ceramic of the invention. The invention is also directed to such a glass. It is obtainable by the above process in step (b). This lithium silicate glass according to the invention comprises the following components:

| Component | wt.-% |
|---|---|
| $SiO_2$ | 64.0 to 75.0, in particular 64.0-73.0 |
| $Li_2O$ | 13.0-17.0 |
| $K_2O$ | 2.0-5.0 |
| $Al_2O_3$ | 0.5-5.0 |
| Nucleating agent | 2.0-5.0 |
| Me(II)O | 0-3.0 | with Me(II)O being selected from at least one of CaO, BaO, MgO and SrO, and which comprises less than 0.1 wt. % of ZnO, and comprises nuclei suitable for formation of lithium metasilicate crystals.

For manufacturing a dental restoration by the hot pressing technique, it is preferred to use a lithium silicate glass ingot according to the invention having nuclei for lithium metasilicate. This ingot is heated to about 700 to 1200° C. to convert it into a viscous state. The heat treatment can be conducted in a special furnace (EP 500®, EP 600®, Ivoclar Vivadent AG). The ingot is embedded in a special investment material. During the heat treatment the ingot will be crystallized. The main crystal phase is then lithium disilicate. The viscous glass ceramic flows under a pressure of 1 to 4 MPa into the cavity of the investment material to obtain the desired shape of the dental restoration. After cooling the investment mould to room temperature the lithium disilicate restoration can be divested by sand blasting. The restoration can be further coated with a glass or a glass ceramic by sintering or a hot pressing technique to obtain the finalized dental restoration with natural aesthetics.

The same hot-pressing technique can be applied to the lithium metasilicate glass ceramic according to the invention which will be converted to lithium disilicate glass ceramic.

A preferred method for converting the lithium metasilicate glass ceramic according to the invention to a lithium disilicate glass ceramic dental restoration by the CAD/CAM technique uses lithium metasilicate glass ceramic blanks, e.g. blocks, having a strength of about 80 to 150 Mpa. These can be easily machined in a CAM unit like Cerec 2® or Cerec (Sirona, Germany). Larger milling machines such as DCS Precimill® (DCS, Switzerland) are also suitable. The block is therefore positioned in the grinding chamber by a fixed or integrated holder. The CAD construction of the dental restoration is done by a scanning process or an optical camera in combination with a software tool. The milling process needs for one unit about 10 to 15 minutes. Copy milling units such as Celay® (Celay, Switzerland) are also suitable for machining the blocks. First, a 1:1 copy of the desired restoration is fabricated in hard wax. The wax model is then mechanically scanned and 1:1 mechanically transmitted to the grinding tool. The grinding process is therefore not controlled by a computer. The milled dental restoration has to be subjected to the third heat treatment to obtain the desired lithium disilicate glass ceramic with high strength and tooth-like color. The product can be further coated with a glass or a glass ceramic by sintering or hot pressing technique to obtain the final dental restoration with natural aesthetics.

The lithium metasilicate glass ceramic according to the invention can also be used for coating a dental restoration. The coating is preferably effected by hot-pressing the lithium metasilicate glass ceramic onto the restoration.

It was surprisingly found that the easily machinable lithium metasilicate glass ceramic according to the invention can be converted by a further heat treatment into a lithium disilicate glass ceramic product having also excellent optical properties. The conversion to a lithium disilicate glass ceramic is associated with a very small linear shrinkage of only about 0.2 to 0.3%, which is almost negligible in comparison to a linear shrinkage of up to 30% when sintering ceramics. The obtained lithium disilicate glass ceramic has not only excellent mechanical properties, such as high strength, but also displays other properties required for a material for dental restorations. It is emphasized that these properties are achieved without the need for ZnO as a component which may be detrimental for specific restorations in view of its strong opalescent effect.

Thus, a product is finally obtained which has all the beneficial mechanical, optical and stability properties making lithium disilicate ceramics attractive for use as dental restorative materials. However, these properties are achieved without the disadvantages of the conventional materials when shaped by using a CAD/CAM based process, in particular the undue wear of the milling and trimming tools.

The invention is explained in more detail below on the basis of Examples.

EXAMPLES

Examples 1 to 8

A total of 8 different lithium metasilicate glass ceramics according to the invention with the chemical compositions given in Table I were prepared using the indicated second heat treatment. The obtained glass ceramics were then converted to the corresponding lithium disilicate glass ceramics using the indicated third heat treatment.

Firstly, samples of the corresponding starting glasses were melted in a platinum-rhodium crucible at a temperature of 1450° C. and for a period of 40 minutes. The glass melt was poured into water and the obtained granules were, after drying, again melted at 1500° C. The glass melts obtained were then poured into graphite moulds to give blocks. After relaxation of the glass blocks at 500 to 600° C. for 10 minutes to 3 hours, they were subjected to the given second heat treatment. Before effecting the third heat treatment, the blocks were checked for their machinability by milling in a CAD-CAM milling machine (i.e. CEREC 3®). Finally, the indicated third heat treatment was conducted. The crystal phases present after the second and third heat treatment were identified by XRD techniques and are given in table I.

Further, the opalescence of the products was visually assessed and the contrast value CR was determined according to BS 5612 (British Standard) using a spectral colorimeter (Minolta CM-3700d). The chemical stability in acetic acid was determined as well as the stability in artificial saliva. The corresponding data are to be found in the following Table II and show in particular the surprising combination of a lack of opalescence together with a high translucence and stability. The composition of the artificial saliva is given in table III.

The data obtained show that the lithium metasilicate glass ceramics according to the invention combine a very good machinability and high edge strength with the easy possibility to convert them by a simple heat treatment into lithium disilicate glass ceramics which have a very high bending strength as well as an excellent chemical durability and good translucence, all of which being properties which make them very attractive as materials useful for the manufacture of dental restorations.

Examples 9 to 12

Four glass ceramics according to the invention were prepared in analogous manner as examples 1 to 8. However, the heat treatment scheme was different. In addition each material was subjected to the schemes referred to as "Cycle A" and "Cycle B" which differ in the temperature used for the crystallization of lithium metasilicate, namely 650° and 700° C., respectively.

Details as to the materials prepared and tested as well as their properties are given in the table IV. It is apparent that the "Cycle B" treatment using a temperature of 700° C. for the crystallization of lithium metasilicate leads to lithium disilicate glass ceramics having excellent strengths.

TABLE III

Composition of artificial saliva

| Component | Amount in mg in a total of 500 ml $H_2O$ |
|---|---|
| NaCl | 125.64 |
| KCl | 963.9 |
| $NH_4Cl$ | 178.0 |
| $CaCl_2 \cdot 2H_2O$ | 227.8 |
| KSCN | 189.2 |
| $CO(NH_2)_2$ | 200.0 |
| $Na_2SO_4 \cdot 10H_2O$ | 336.2 |
| $NaHCO_3$ | 630.8 |
| $KH_2PO_4$ | 654.5 |

TABLE I

| | Example | | | | | | | |
|---|---|---|---|---|---|---|---|---|
| | 1 | 2 | 3 | 4 | 5 | 6 | 7 | 8 |
| Molar ratio | | | | | | | | |
| $SiO_2:Li_2O$ | 2.39:1 | 2.39:1 | 2.4:1 | 2.39:1 | 2.39:1 | 2.39:1 | 2.39:1 | 2.39:1 |
| $Al_2O_3:K_2O$ | 1:1.0 | 1:1.0 | 1:1.2 | 1:1.20 | 1:1.35 | 1:1.50 | 1:1.70 | 1:1.30 |
| | wt.-% (Mol %) | wt.-% (Mol %) | wt.-% (Mol %) | wt.-% (Mol %) | wt.-% (Mol %) | wt.-% (Mol %) | wt.-% (Mol %) | wt.-% (Mol %) |
| $SiO_2$ | 72.21 (66.12) | 70.64 (65.62) | 70.52 (65.52) | 70.78 (65.57) | 70.78 (65.56) | 70.78 (65.56) | 70.78 (65.55) | 70.78 (65.29) |
| $K_2O$ | 3.16 (1.85) | 3.09 (1.83) | 3.81 (2.26) | 3.76 (2.22) | 3.96 (2.34) | 4.16 (2.46) | 4.36 (2.58) | 3.36 (1.98) |
| $Li_2O$ | 14.99 (27.60) | 14.68 (27.43) | 14.64 (27.35) | 14.7 (27.38) | 14.7 (27.38) | 14.7 (27.37) | 14.7 (27.37) | 14.7 (27.26) |
| $Al_2O_3$ | 3.45 (1.86) | 3.38 (1.85) | 3.35 (1.83) | 3.38 (1.85) | 3.18 (1.74) | 2.98 (1.63) | 2.78 (1.52) | 2.78 (1.51) |
| $P_2O_5$ | 3.28 (1.27) | 3.21 (1.26) | 3.2 (1.26) | 3.21 (1.26) | 3.21 (1.26) | 3.21 (1.26) | 3.21 (1.26) | 3.21 (1.25) |
| $ZrO_2$ | 2.91 (1.30) | 3.00 (1.36) | 2.5 (1.13) | 1.8 (0.81) | 1.8 (0.81) | 1.80 (0.81) | 1.8 (0.81) | 1.8 (0.81) |
| $CeO_2$ | | 1.88 (0.61) | 1.86 (0.60) | 2.00 (0.65) | 2.00 (0.65) | 2.00 (0.65) | 2.00 (0.65) | 2.00 (0.65) |
| $V_2O_5$ | | 0.12 (0.04) | 0.12 (0.04) | 0.07 ((0.02) | 0.07 ((0.02) | 0.07 (0.02) | 0.07 (0.02) | 0.07 (0.02) |
| $MnO_2$ | | | | 0.03 (0.02) | 0.03 (0.02) | 0.03 (0.02) | 0.03 (0.02) | 0.03 (0.02) |
| $Er_2O_3$ | | | | 0.12 (0.017) | 0.12 (0.017) | 0.12 (0.17) | 0.12 (0.017) | 0.12 (0.017) |
| MgO | | | | 0.15 (0.21) | 0.15 (0.21) | 0.15 (0.21) | 0.15 (0.21) | 0.15 (0.21) |
| CaO | | | | | | | | 1.00 (0.99) |
| Crystalline phases after: | | | | | | | | |
| Second heat treatment: 20'/650° C. | $Li_2SiO_3$ $Li_2Si_2O_5$ * | $Li_2SiO_3$ $Li_2Si_2O_5$ * | $Li_2SiO_3$ | $Li_2SiO_3$ | | $Li_2SiO_3$ | $Li_2SiO_3$ | $Li_2SiO_3$ $Li_2Si_2O_5$ |
| Third heat treatment: 10'/850° C. | $Li_2Si_2O_5$ $Li_3PO_4$* | $Li_2Si_2O_5$ $Li_3PO_4$* | $Li_2Si_2O_5$ $Li_3PO_4$* | $Li_2Si_2O_5$ $Li_3PO_4$* | $Li_2Si_2O_5$ $Li_3PO_4$* | $Li_2Si_2O_5$ $Li_3PO_4$* | $Li_2Si_2O_5$ $Li_3PO_4$* | $Li_2Si_2O_5$ $Li_3PO_4$* |

TABLE II

| | Example | | | | |
|---|---|---|---|---|---|
| | 1 | 2 | 3 | 4 | 6 |
| CR-Value BS-5612 (1978) | 40.4 | 37.0 | 50.0 | 59.3 | 58.8 |
| Opalescence | No | No | No | No | No |
| Chemical stability in Acetic acid (24 h/ 80° C., mass loss in µg/cm²) | 9 | 18 | 48 | 3 | 9 |
| Chemical stability in Saliva (7 d/60° C., mass loss in µg/cm²) | 13 | 17 | 28 | 27 | 17 |

TABLE IV

| | Example | | | |
|---|---|---|---|---|
| | 9 | 10 | 11 | 12 |
| $SiO_2$ | 74.37 | 72.89 | 72.21 | 71.40 |
| $K_2O$ | 3.26 | 3.18 | 3.16 | 3.13 |
| $Li_2O$ | 15.44 | 15.13 | 14.99 | 14.79 |
| $Al_2O_3$ | 3.55 | 3.48 | 3.45 | 3.13 |
| $P_2O_5$ | 3.38 | 3.31 | 3.28 | 3.22 |
| $ZrO_2$ | 0.00 | 2.01 | 2.91 | 4.05 |
| | All values above in wt.-% | | | |
| $SiO_2:Li_2O$ | 2.39 | 2.40 | 2.39 | 2.40 |
| Cycle A: | (1) 500° C./10 min + (2) 650° C./20 min + (3) 850° C./10 min *) | | | |
| Biaxial Flexural Strength/MPa | 786 +/− 92 | 515 +/− 54 | 522 +/− 82 | 479 +/− 36 |
| Contrast Ratio | 0.80 | 0.56 | 0.43 | 0.36 |
| Cycle B: | (1) 500° C./10 min + (2) 700° C./20 min + (3) 850° C./10 min *) | | | |

TABLE IV-continued

| | Example | | | |
|---|---|---|---|---|
| | 9 | 10 | 11 | 12 |
| Biaxial Flexural Strength/MPa | 828 +/− 104 | 659 +/− 75 | 608 +/− 90 | 694 +/− 113 |
| Contrast Ratio | 0.83 | 0.63 | 0.53 | 0.41 |

*) (1) Nucleation in the glass
(2) Crystallization of Li-Metasilicate
(3) Crystallization of Li-Disilicate from Li-Metasilicate

What is claimed is:

1. A lithium silicate glass ceramic for dental restorations, wherein the lithium silicate glass ceramic comprises:
    $SiO_2$ from 64 to 75 wt %; and
    a main crystalline phase of lithium metasilicate;
    wherein the glass ceramic is suitable to be subjected to a heat treatment to convert the main crystalline phase from lithium metasilicate to lithium disilicate and the glass ceramic has a biaxial flexural strength of between 450-820 MPa.

2. The lithium silicate glass ceramic of claim 1, comprising 64 to 73 wt % of $SiO_2$.

3. The lithium silicate glass ceramic of claim 1, wherein the lithium silicate glass ceramic is shaped into a dental restoration by machining or pressing.

4. The lithium silicate glass ceramic of claim 3, wherein machining comprises grinding, trimming, or milling.

5. The lithium silicate glass ceramic of claim 1, wherein the dental restoration is an inlay, an onlay, a bridge, an abutment, a facing, a veneer, a facet, a crown, a partial crown, a framework or a coping.

* * * * *